United States Patent [19]

Ziccardi

[11] 4,193,068
[45] Mar. 11, 1980

[54] HEMORRHAGE ALARMS

[76] Inventor: John J. Ziccardi, R.D. #1, Evans City, Pa. 16033

[21] Appl. No.: 784,147

[22] Filed: Apr. 4, 1977

Related U.S. Application Data

[63] Continuation-in-part of Ser. No. 667,390, Mar. 16, 1976, abandoned.

[51] Int. Cl.$^2$ ...................... G08B 21/00; H01H 35/00
[52] U.S. Cl. ..................................... 340/604; 128/638; 200/61.04; 200/DIG. 2; 200/52 R
[58] Field of Search ............... 340/235, 242, 604, 605; 128/2 R; 200/61.04, 61.05, 61.06, 246, 52 R, DIG. 2

[56] References Cited

U.S. PATENT DOCUMENTS

| | | | |
|---|---|---|---|
| 2,043,857 | 6/1936 | Montgomery | 340/242 |
| 2,258,554 | 10/1941 | Heyer et al. | 340/235 X |
| 2,326,557 | 8/1943 | Pierce | 340/242 X |
| 2,432,367 | 12/1947 | Andresen | 340/242 X |
| 2,749,536 | 6/1956 | Sperling | 340/242 |
| 3,245,068 | 4/1966 | Wegryn et al. | 340/235 |

FOREIGN PATENT DOCUMENTS

| | | | |
|---|---|---|---|
| 1449824 | 7/1966 | France | 340/235 |
| 380383 | 9/1932 | United Kingdom | 200/61.04 |
| 930454 | 7/1963 | United Kingdom | 340/235 |

Primary Examiner—John W. Caldwell, Sr.
Assistant Examiner—Daniel Myer
Attorney, Agent, or Firm—Buell, Blenko & Ziesenheim

[57] ABSTRACT

A hemorrhage alarm system having an electrically operated signal device, a source of electrical current, a circuit connecting said current source and signal device, a normally open switch in said circuit and a means swelling on contact with blood and body fluid acting on said switch to close it on contact with blood and body fluid.

5 Claims, 9 Drawing Figures

Series-Parallel Circuit For Buzzer And Lamp Signals (Multiple Sensors)

Installation Of System In Hospital

HEMORRHAGE ALARMS

This application is a continuation-in-part of my copending application Ser. No. 667,390, filed Mar. 16, 1976 abandoned.

This invention relates to hemorrhage alarms and particularly to an alarm and an activating sensor for detecting and rendering an alarm when a patient loses blood beyond a pre-determined amount.

The problem of excessive bleeding and hemorrhage following wounds or surgical processes is well known. The problem of how to timely detect such bleeding has long faced the medical profession without a simple reliable solution. There have been in the past signal devices for warning of excessive bleeding. For example Heyer et al. U.S. Pat. No. 2,258,554 issued in 1941 provided a device in which two spaced electrical contacts were held apart by a gauze tube, which, when wetted by blood or body fluid was designed to act as a conductor and bridge the electrical circuit to set off an alarm. In 1966, U.S. Pat. No. 3,245,068 issued to Wegryn et al. for a body fluid detecting device which depended upon absorption of fluid in a blotting paper between two conductors acting to transmit current. Thus in both of these prior art devices the conduction of current was dependent upon the body fluid acting as a conductor for an electrical current. These devices were operable and would serve the purpose for which they were designed in most instances, however, they did not have inherent drawbacks in the fact that they depended upon the body fluid acting as an electrolyte and being the only means of closing the circuit contact. These devices have not met with general acceptance and the surgical art at this late date has no reliable means of detecting hemorrhage, see *Nursing* '75, February, page 25.

I have invented a hemorrhage detector and alarm which provides for making positive mechanical contact between two points in an electrical circuit when a predetermined amount of blood or body fluid is released into a surgical dressing.

I provide an electrically operated signal device, a source of electrical current, a circuit connecting said source of electrical current and said electrically operated alarm, a normally open switch means in said circuit and means swelling on contact with body fluid and blood acting on said switch means to close the same when a sufficient amount of fluid has contacted the swelling means. Preferably the means swelling on contact with body fluid and blood is a dessicated sponge or a dessicated gelatin layer which on contact with body fluids and bloods swells a multiple of its normal thickness. The signal device may be an alarm such as a bell or buzzer, or a light or a combination of a bell or buzzer and a light.

In the foregoing general outline of my invention I have set out certain objects, purposes and advantages of my invention. Other objects, purposes and advantages of this invention will be apparent from a consideration of the following description and the accompanying drawings in which.

Figure 4:
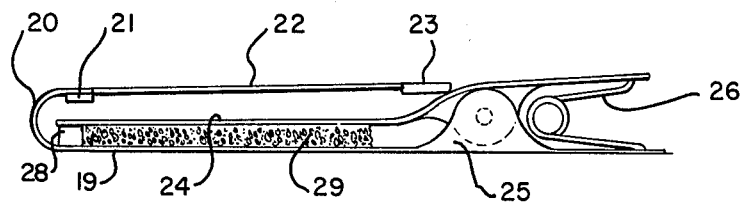
FIG. 4 is a side elevational view of the switch of FIG. 3 with a dessicated sponge in place.

Referring to the drawings I have illustrated a person 10 having two lesions covered by surgical dressings 11 and 12. Each surgical dressing has a normally open switch 13 with a dessicated sponge 14 as illustrated in FIG. 4. Each switch is connected to a power source 15 and a buzzer 16 mounted in an alarm box 17 mounted on a neck band 18 worn around the patient's neck.

Figure 1:
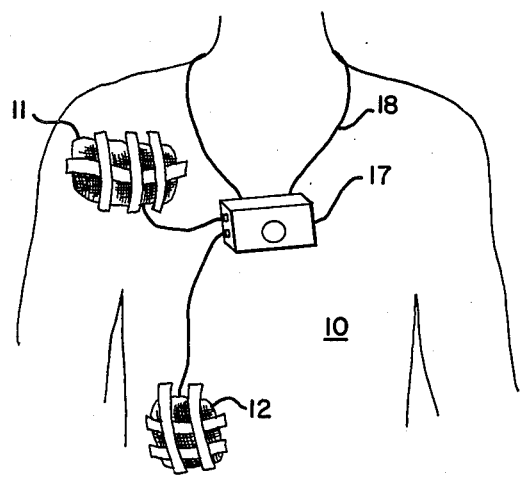
FIG. 1 is a front elevational view of a person having two lesions with the signal system of my invention.
Figure 3:
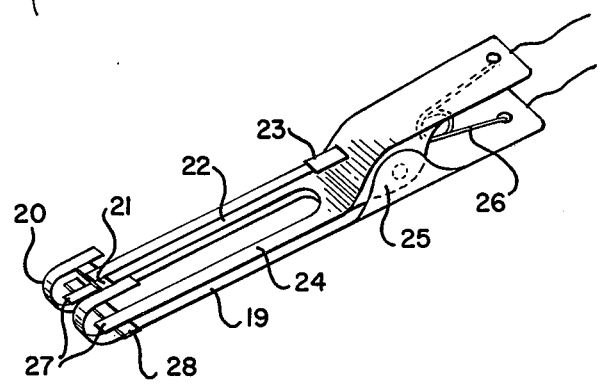
FIG. 3 is an isometric view of a normally open switch as used in my invention.
Figure 2:
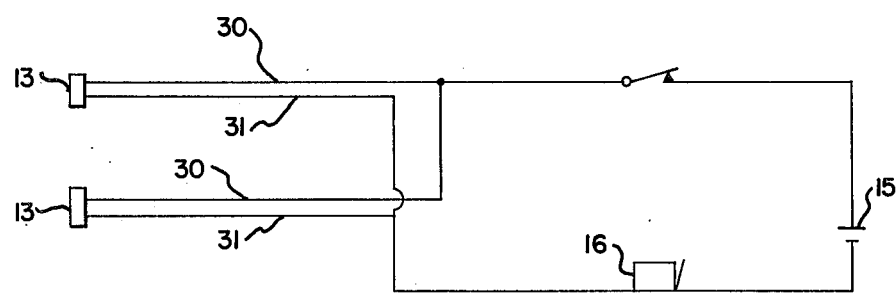
FIG. 2 is a schematic wiring diagram of the system of FIG. 1.
Figure 5:
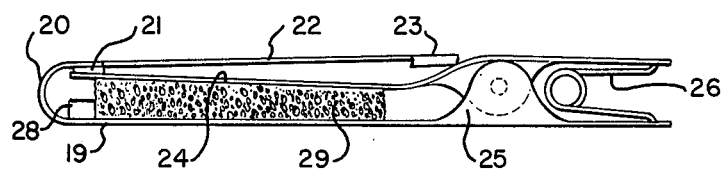
FIG. 5 is a side elevational view of the switch of FIG. 4 with the sponge expanded after wetting.

The switch illustrated in FIGS. 3, 4 and 5 is made up of a base conductor 19 having a U-shaped end 20 with contact bar 21 mounted thereon. A guard 22 is mounted at one end on the contact bar to extend parallel to the base conductor. The guard 22 is insulated at its free end 23 and is designed to protect the moving conductor 24 from the surgical dressing. The movable conductor 24 is pivoted on upstanding arms 25 on the base conductor and is insulated therefrom by an insulating film. A spring 26 urges the movable conductor about the pivot so that the contact end 27 rests on insulator 28 on the base conductor. A dessicated sponge 29 is placed between the base conductor 19 and the movable conductor 24. The switch assembly is connected to the power source 15 and buzzer 16 by leads 30 and 31 as shown in FIG. 2.

When the switch assembly is placed in a surgical dressing over a body lesion, the presence of substantial amounts of blood or body fluids will cause sponge 29 to rapidly absorb the liquid and to swell, overcoming spring 26 and forcing the moving conductor 24 to pivot so that contacts 27 engage contact bar 21 and pass current through the energize buzzer 16.

Figure 6:
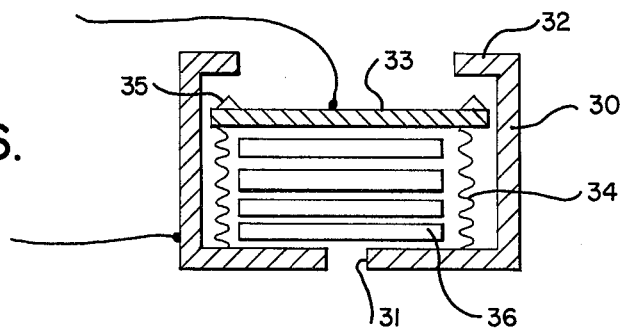
FIG. 6 is a section through a second embodiment of normally open switch according to my invention.

In FIG. 6 I have illustrated another form of switch having an outer short cylindrical housing 30 having a perforate bottom 31 and an inturned top flange 32. A contact disc 33 is mounted within the housing 30 and held away from the flange 32 by a light spring 34 insulated from the disc 33. The disc 33 is provided with vertical contact points 35 spaced apart around its periphery. The area between bottom 31 and disc 33 is filled with dessicated gelatin 36 or alternately by a dessicated sponge. When blood or body fluid enters into housing 30 the gelatin or sponge swells forcing points 35 into contact with flange 32 completing the circuit through the switch.

Figure 7:
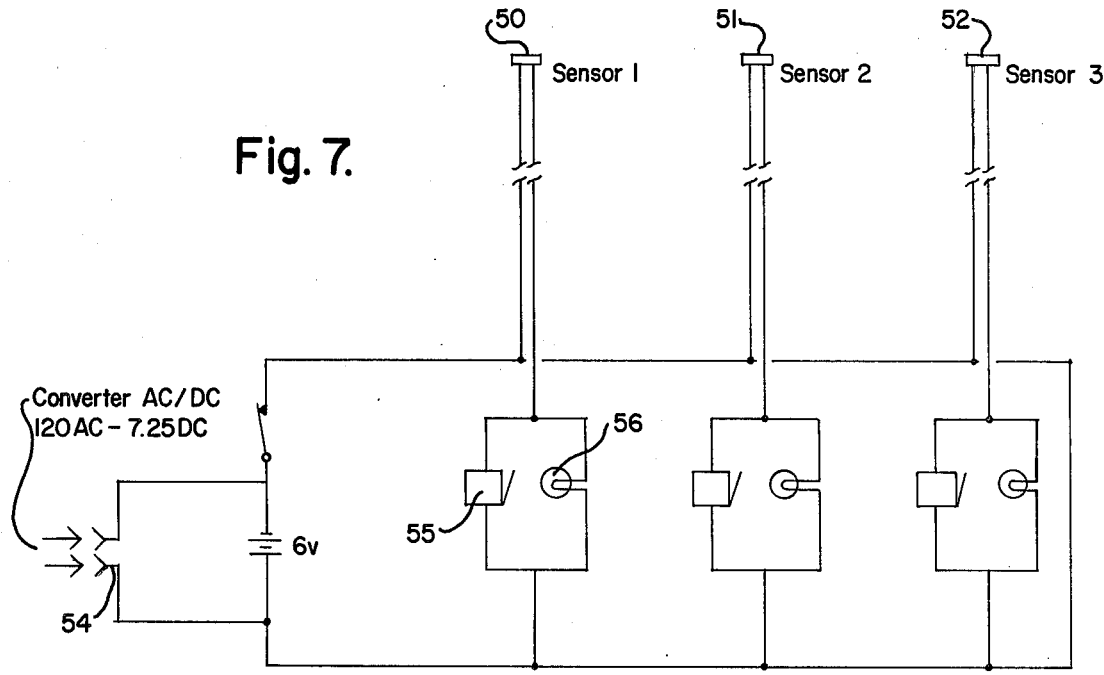
FIG. 7 is a schematic circuit of several sensors and alarms for use in a hospital.
Figure 9:
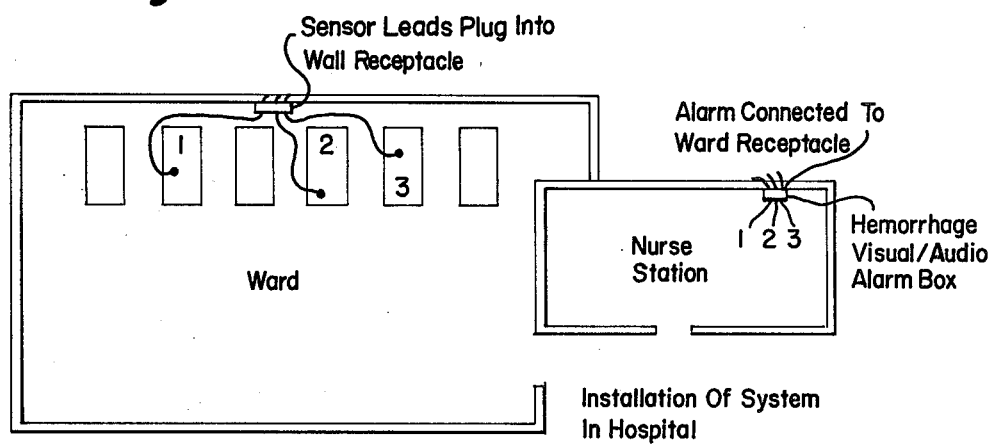
FIG. 9 is a plan view of a hospital ward and nurse station with the invention included therein.

In FIG. 7 I have illustrated a wiring arrangement for a plurality of sensors 50, 51 and 52 on three separate patients all connected to a common power source 54 and each having a separate alarm buzzer 55 and indicator light 56 to indicate to the hospital attendant the particular patient having excessive bleeding or body fluid loss.

Figure 8:
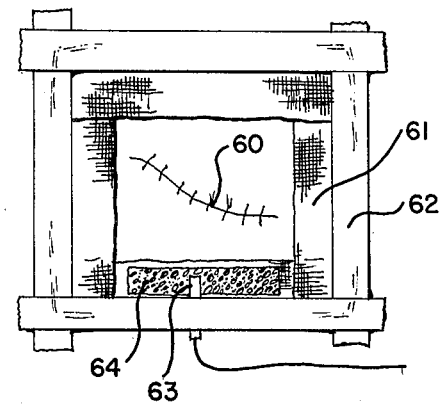
FIG. 8 is a plan view of another embodiment of this invention.

In FIG. 8 I have illustrated another arrangement for use of this invention in which a wound 60, instead of being covered by a dressing is surrounded by a dam 61 of gauze, held in place by peripheral tape 62. A sensor 63 and activating sponge 64 are embedded in or on one or more sides of dam 61. In the event the wound opens and fluid flows therefrom it will be collected in the gauze dam 61 and cause sponge 64 to swell, activating sensor 63 (in the form shown in FIGS. 4 and 5) as described above.

While I have illustrated and described certain presently preferred embodiments and practices of my invention in the foregoing specification, it will be obvious that this invention can be otherwise embodied within the scope of the following claims.

I claim:

1. A hemorrhage alarm system comprising an electrically operated signal device, a source of electrical current, a circuit connecting said source of electrical current and said signal device, mechanical switch means in said circuit having two separate elongate switch members, one of said switch members generally surrounding the other on at least two sides opposite of the other switch member in its direction of movement whereby a wound dressing cannot interfere with the function of the switch, contact means on one end of said other switch member, corresponding contact means on one side of said other switch member, said other switch member being pivotally connected to said one switch member intermediate their lengths and movable only between said at least two sides within the surrounding one switch member between an open spaced apart position in which said contact means on the other switch member is spaced from the contacts on said one of said two sides of the one switch member and a closed position in which the two contacts are engaged, resilient means normally holding said contacts on said switch members apart, and means between said other switch member and the other side of said two sides of said one switch member swelling on contact with blood and body fluid acting on said switch mechanically to close the two normally spaced apart contacts by moving said other switch member toward said one switch member and overcoming the resilient means on contact with sufficient blood and body fluid to swell the same.

2. A hemorrhage alarm system as claimed in claim 1 wherein the swelling means is a compressed dessicated sponge.

3. A hemorrhage alarm system as claimed in claim 1 wherein the swelling means is dessicated gelatin.

4. A hemorrhage alarm system comprising an electrically operated signal device, a source of electrical current, a circuit connecting said source of electrical current and said signal device, mechanical switch means in said circuit having two contacts on two separate switch members, one of said switch members generally surrounding the other on at least two sides whereby a wound dressing cannot interfere with the function of the switch, said other switch member being movable only between said at least two sides within the surrounding one switch member between an open spaced apart position and a closed position in which the two contacts are engaged, resilient means normally holding said switch members apart, and means between said switch members swelling on contact with blood and body fluid acting on said switch mechanically to close the two normally spaced apart contacts by moving said other switch member toward said one switch member and overcoming the resilient means on contact with sufficient blood and body fluid to swell the same wherein the said one of said switch members includes an elongated base conductor having a generally U-shaped tip at one end, bent back over itself to form a parallel guard; contact means on said conductor adjacent said U-shaped tip; an elongated movable conductor pivoted to said base conductor and having an end adapted to contact the contact means on the base plate, resilient means biasing said movable conductor out of contact with said contact means and swelling means between said base conductor and movable conductor swelling on contact with blood and body fluids to force the blade against the contact means.

5. A hemorrhage alarm system as claimed in claim 4 wherein guard means extends over the movable conductor to prevent a surgical dressing from limiting its movement toward the contact points.

* * * * *